(12) United States Patent
Liu et al.

(10) Patent No.: US 9,879,343 B2
(45) Date of Patent: Jan. 30, 2018

(54) DETECTION SYSTEM FOR DETECTING SERVICE LIFE OF BAFFLE MECHANISM IN A CHAMBER FOR VACUUM COATING

(71) Applicants: Boe Technology Group Co., Ltd., Beijing (CN); Beijing Boe Display Technology Co., Ltd., Beijing (CN)

(72) Inventors: Xiaowei Liu, Beijing (CN); Yao Liu, Beijing (CN); Xiangqian Ding, Beijing (CN); Jinchao Bai, Beijing (CN)

(73) Assignees: BOE TECHNOLOGY GROUP CO., LTD., Beijing (CN); BEIJING BOE DISPLAY TECHNOLOGY CO. LTD., Beijing (CN)

( * ) Notice: Subject to any disclaimer, the term of this patent is extended or adjusted under 35 U.S.C. 154(b) by 36 days.

(21) Appl. No.: 14/496,062

(22) Filed: Sep. 25, 2014

(65) Prior Publication Data
US 2015/0323483 A1    Nov. 12, 2015

(30) Foreign Application Priority Data
May 6, 2014   (CN) .......................... 2014 1 0188927

(51) Int. Cl.
  *C23C 14/54*   (2006.01)
  *C23C 16/52*   (2006.01)
  (Continued)

(52) U.S. Cl.
  CPC ............ *C23C 16/52* (2013.01); *C23C 14/545* (2013.01); *C23C 14/564* (2013.01);
  (Continued)

(58) Field of Classification Search
  None
  See application file for complete search history.

(56) References Cited

U.S. PATENT DOCUMENTS

| | | | | |
|---|---|---|---|---|
| 3,031,617 A | * | 4/1962 | Paquette | G01B 7/02 324/601 |
| 3,278,843 A | * | 10/1966 | Deming | C23C 14/545 118/665 |
| 3,775,277 A | * | 11/1973 | Pompei | C23C 14/545 204/192.13 |
| 5,382,911 A | * | 1/1995 | Cotler | C23C 16/52 702/65 |

(Continued)

FOREIGN PATENT DOCUMENTS

| CN | 101078613 | 11/2007 |
|---|---|---|
| CN | 101958232 | 1/2011 |
| JP | 2010-236040 | 10/2010 |

OTHER PUBLICATIONS

Office action from Chinese Application No. 201410188927.2 dated Oct. 29, 2015.

*Primary Examiner* — Binu Thomas
(74) *Attorney, Agent, or Firm* — Calfee, Halter & Griswold LLP

(57) ABSTRACT

A detection device includes a chamber for vacuum coating, a capacitance measurement device and a baffle mechanism located in the chamber. The baffle mechanism is a closed structure encompassed by a number of baffle walls, wherein at least one baffle wall includes a fixed baffle plate and a moveable baffle plate. The moveable baffle plate is pivotable about the fixed baffle plate. The moveable baffle plate, after pivoting, may get parallel with an adjacent baffle wall. The adjacent baffle wall and the moveable baffle plate are respectively connected to the capacitance measurement device, and the capacitance measurement device is used to measure the capacitance between the adjacent baffle wall and the moveable baffle plate. The detection device may accurately detect the service life of the baffle mechanism and achieve precise management of the apparatus.

10 Claims, 2 Drawing Sheets

(51) Int. Cl.
  *C23C 2/14* (2006.01)
  *G01N 27/22* (2006.01)
  *C23C 16/455* (2006.01)
  *C23C 16/44* (2006.01)
  *G01R 27/26* (2006.01)
  *C23C 14/56* (2006.01)
  *H01L 21/67* (2006.01)
  *H01J 37/32* (2006.01)
  *G01B 7/06* (2006.01)

(52) U.S. Cl.
  CPC .... *C23C 16/4401* (2013.01); *C23C 16/45589* (2013.01); *C23C 16/45591* (2013.01); *G01N 27/228* (2013.01); *G01R 27/26* (2013.01); *C23C 2/14* (2013.01); *G01B 7/085* (2013.01); *G01B 7/105* (2013.01); *H01J 37/32568* (2013.01); *H01L 21/67253* (2013.01)

(56) References Cited

U.S. PATENT DOCUMENTS

| | | | | |
|---|---|---|---|---|
| 6,132,805 A | * | 10/2000 | Moslehi | C23C 14/22 118/720 |
| 6,543,459 B1 | * | 4/2003 | Annapragada | C23C 16/4405 134/1.1 |
| 6,616,818 B2 | * | 9/2003 | Gibson | C23C 14/044 118/504 |
| 2002/0179013 A1 | * | 12/2002 | Kido | C23C 14/12 118/718 |
| 2005/0235917 A1 | * | 10/2005 | Fordemwalt | C23C 16/4407 118/723 R |
| 2012/0216955 A1 | * | 8/2012 | Eto | C23C 16/4404 156/345.51 |
| 2014/0299577 A1 | * | 10/2014 | Chung | C23C 16/4401 118/712 |

* cited by examiner

DETECTION SYSTEM FOR DETECTING SERVICE LIFE OF BAFFLE MECHANISM IN A CHAMBER FOR VACUUM COATING

RELATED APPLICATIONS

The present application claims the benefit of Chinese Patent Application No. 201410188927.2, filed May 6, 2014, the entire disclosure of which is incorporated herein by reference.

BACKGROUND OF THE DISCLOSURE

1. Field of the Disclosure

The present disclosure relates to technical field of vacuum coating, and particularly to a detection device for detecting a service life of a baffle mechanism in a vacuum coating apparatus.

2. Description of the Prior Art

At present, vacuum coating technology is extensively applied to various fields of industrial production. Particularly when applied to fields such as Thin Film Transistor-Liquid Crystal Display (TFT-LCD) and Organic Light Emitting Diode (OLED), a vacuum apparatus may generate extra thin film deposition. As is commonly known in the technical field of vacuum coating, a vacuum coating apparatus includes a vacuum cavity or chamber and a coating material generating device in the vacuum cavity or chamber for generating coating material that is to be deposited as a thin film. In order to prevent the extra-generated thin film from polluting a vacuum cavity, a baffle mechanism is usually provided in the vacuum cavity so that the extra-generated thin film will deposit on the baffle mechanism. Then the baffle mechanism is cleaned regularly to effectively protect the vacuum cavity. Such coating manner is extensively applied to various vacuum apparatuses such as apparatuses for Physical Vapor Deposition (PVD), Chemical Vapor Deposition (CVD), Dry Etching, and sputter coating.

The service life of the baffle mechanism, as an important part of the vacuum apparatus, depends on a thickness of the adhered thin film. The service life of the baffle mechanism can be effectively detected only when the thickness of the adhered thin film is accurately mastered. However, currently human experience cannot suffice to accurately judge the expiration of the service life of the baffle mechanism and to perform precise management of the baffle mechanism service life. If the baffle mechanism is replaced in advance and sent to a dedicated manufacturer for cleaning, unnecessary operation cost will be caused; if the baffle mechanism is replaced when it expires, a qualified rate of products will be affected.

Therefore, with respect to the above drawbacks, it is desirable to provide a detection device which is capable of accurately detecting the service life of the baffle mechanism, achieving precise apparatus management and reducing the operation cost.

SUMMARY OF THE DISCLOSURE

The technical problem to be solved by the present disclosure is to provide a detection device which is capable of accurately detecting the service life of the baffle mechanism, achieving precise apparatus management and reducing the operation cost To solve the above technical problem, the present disclosure provides a detection device comprising: a chamber for vacuum coating; a capacitance measurement device and a baffle mechanism located in the chamber. The baffle mechanism is a closed structure encompassed by a plurality of baffle walls, wherein at least one baffle wall comprises a fixed baffle plate and a moveable baffle plate. The moveable baffle plate is pivotable about the fixed baffle plate. The moveable baffle plate, after pivoting, may get parallel with an adjacent baffle wall. The adjacent baffle wall and the moveable baffle plate are respectively connected to the capacitance measurement device, and the capacitance measurement device is used to measure the capacitance between the adjacent baffle wall and the moveable baffle plate.

The baffle mechanism is in shape of a cube. The fixed baffle plate and the moveable baffle plate are both located at the top or bottom of the cube. The moveable baffle plate, after pivoting by a 90° angle about the fixed baffle plate, gets parallel with the adjacent baffle wall.

An edge of the moveable baffle plate is provided with a first connection portion and a second connection portion. During closing the baffle mechanism, the moveable baffle plate is pivoted to connect the first connection portion thereof to an end of the fixed baffle plate, and the second connection portion to another end of the fixed baffle plate.

A seal strip is disposed on the first connection portion, and located at a slit between the fixed baffle plate and the moveable baffle plate.

The first connection portion and the second connection portion are both made of an insulative material.

The moveable baffle plate is rectangular, and the number of the moveable baffle plates is one or plural.

The adjacent baffle wall and the moveable baffle plate are respectively connected to the capacitance measurement device via a lead wire.

The capacitance measurement device is a multimeter, a capacitance meter or an electrical bridge testing instrument for measuring the capacitance.

A thin film is deposited inside the baffle wall.

The above technical solution of the present disclosure achieves the following advantages: the baffle mechanism of the detection device of the present disclosure is a closed structure encompassed by a plurality of baffle walls, wherein at least one baffle wall comprises a fixed baffle plate and a moveable baffle plate. The moveable baffle plate is pivotable about the fixed baffle plate. The moveable baffle plate, after pivoting, may get parallel with an adjacent baffle wall. The adjacent baffle wall and the moveable baffle plate are respectively connected to the capacitance measurement device, and the capacitance measurement device is used to measure the capacitance between the adjacent baffle wall and the moveable baffle plate. The detection device may accurately detect the service life of the baffle mechanism and achieve precise management of the apparatus. The detection device is simple in structure and may not greatly increase the manufacture and operation costs. The precise management of the service life of the baffle mechanism may be performed without opening the chamber, thus the operation cost of apparatuses in production line may be effectively reduced.

DETAILED DESCRIPTION OF THE PRESENT DISCLOSURE

Embodiments of the present disclosure will be further described in detail with reference to the figures. The following embodiments are used to illustrate the present disclosure, not to limit the scope of the present disclosure.

In the specification, unless otherwise specified, "a plurality of" means two or more; orientations or positional relationships indicated by the terms such as "up", "down", "left", "right", "in", "out", "front end", "rear end", "leading portion", "trailing portion" are based on orientations or positional relationships shown in the accompanying drawings, are merely used to facilitate the description of the present disclosure and simplify the description, but do not indicate or imply that the intended device or elements must have a particular orientation and are configured and operated in a particular orientation. Therefore, the orientations or positional relationships should not be construed to limit the present disclosure. Besides, the terms "first", "second", "third" and the like are only used for illustration purpose and cannot be understood as indicating or implying relative significance.

In the specification, unless specified or limited otherwise, terms "mount", "connect" and "couple" should be understood in a broad sense, for example, the connection may be either fixed connection or detachable connection or unitary connection; the connection may be either mechanical connection or electrical connection; the connection may be direct connection or indirect connection via an intermediate medium. Those having ordinary skill in the art appreciate that specific meaning of the above terms in the present disclosure may be understood according to specific situations.

Figure 1:
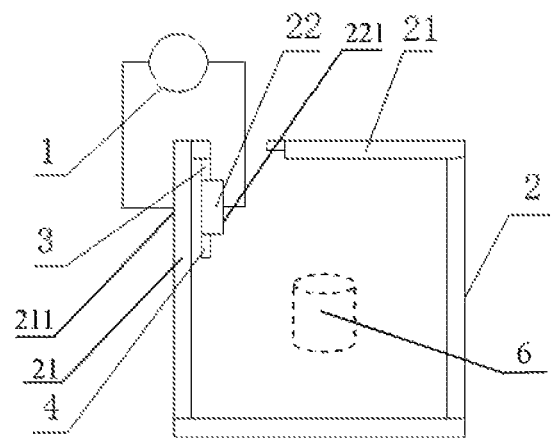
FIG. 1 is a structural schematic view of a detection device according to a first embodiment of the present disclosure.
Figure 2:
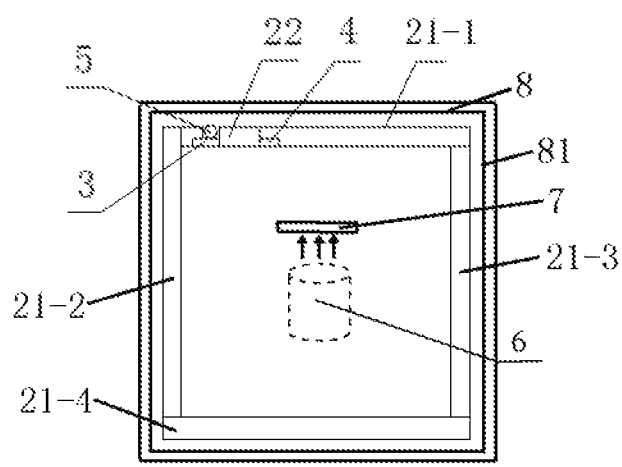
FIG. 2 is a schematic view showing an operation state of a detection device according to the first embodiment of the present disclosure.

As shown in FIG. 1 and FIG. 2, a detection device according to an embodiment of the present disclosure comprises a chamber 8 with an inner wall 81 for vacuum coating, a capacitance measurement device 1 and a baffle mechanism 2 located in the chamber. A coating material generating device 6 is disposed inside the chamber 8. The baffle mechanism 2 is a closed structure encompassed by a plurality of baffle walls 21-1, 21-2, 21-3, 21-4, wherein at least one baffle wall 21-1 comprises a fixed baffle plate 21 and a moveable baffle plate 22. The moveable baffle plate 22 is pivotable about the fixed baffle plate 21. The moveable baffle plate 22, after pivoting, may get parallel with an adjacent baffle wall. The adjacent baffle wall and the moveable baffle plate 22 are respectively connected to the capacitance measurement device 1, and the capacitance measurement device 1 is outside of the baffle mechanism 2 and used to measure the capacitance between the adjacent baffle wall and the moveable baffle plate 22. An object 7 to be coated is positioned between the baffle mechanism 2 and the coating material generating device 6.

The detection device is simple in structure and may not greatly increase the manufacture and operation costs. The precise management of the service life of the baffle mechanism 2 may be performed without opening the chamber, thus the operation cost of apparatuses in production line may be effectively reduced.

For instance, a measurement window is provided at the original baffle mechanism 2, namely, an independent and pivotally moveable baffle 22 is provided at a junction of two baffle walls. When the apparatus is idle, the moveable baffle plate 22 is pivoted to a position parallel with the adjacent baffle wall (as shown in FIG. 1); a voltage is applied to a side 221 of the moveable baffle plate 22 away from the adjacent baffle wall and a backside 211 of the adjacent baffle wall; the capacitance between the moveable baffle plate 22 and the adjacent baffle wall is measured by the capacitance measurement device 1; a spacing between the moveable baffle plate 22 and adjacent baffle wall after coating is calculated according to a capacitance calculating formula $C=\in S/d$, wherein $\in$ is a dielectric constant of a medium between polar plates, S is a polar plate area, and d is a distance between polar plates. Since thin film deposits inside the baffle wall, a thickness of the thin film already adhered on the baffle mechanism 2 may be calculated by comparing the resultant spacing with a spacing between the moveable baffle plate 22 and the adjacent baffle wall before the coating.

The service life of the baffle mechanism 2 depends on the thickness of the adhered thin film. The thickness of the thin film may be calculated by measuring the capacitance between the moveable baffle plate 22 and the adjacent baffle wall, thus a precise service life of the baffle mechanism 2 may be calculated and evaluated without opening the chamber. Upon coating, the independent moveable baffle plate 22 may be pivoted to be closed (as shown in FIG. 2), thus achieving integrity, simple structure and convenient operation of the baffle mechanism 2.

Figure 3:
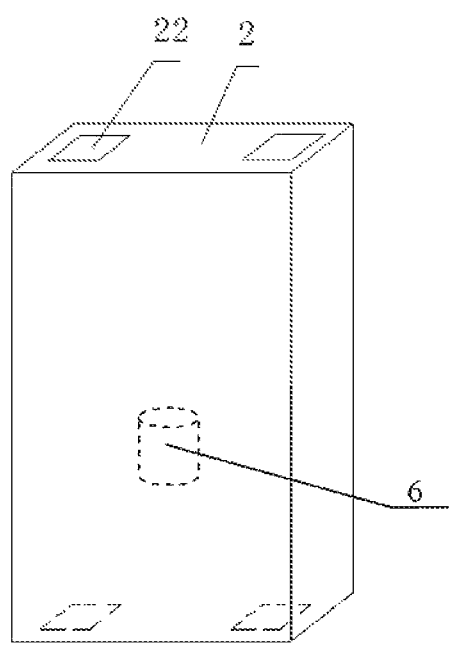
FIG. 3 is a perspective view of a detection device according to a second embodiment of the present disclosure.

As shown in FIG. 3, preferably, the baffle mechanism 2 is in shape of a cube. The fixed baffle plate 21 and the moveable baffle plate 21 are both located at the top or bottom of the cube. The moveable baffle plate 22, after pivoting by a 90° angle about the fixed baffle plate 21, gets parallel with the adjacent baffle wall (as shown in FIG. 1).

In addition, according to actual needs of the coating apparatus, the shape of the baffle mechanism 2 is not limited to this, and other closed structures for preventing thin film deposition from polluting the chamber all fall within the protection scope of the present disclosure. For example, the baffle mechanism 2 may be a cylinder or an irregular body.

As shown in FIG. 2, to prevent thin film penetration between the fixed baffle plate 21 and the moveable baffle plate 22 upon vacuum coating, an edge of the moveable baffle plate 22 is provided with a first connection portion 3 and a second connection portion 4. During closing the baffle mechanism 2, the moveable baffle plate 22 is pivoted to connect the first connection portion 3 thereof to an end of the fixed baffle plate 21, and the second connection portion 4 to another end of the fixed baffle plate 21 hermetically, thereby preventing leakage.

Optionally, a seal strip 5 is disposed on the first connection portion 3, and located at a slit between the fixed baffle plate 21 and the moveable baffle plate 22 to achieve prevention of leakage. Meanwhile, an edge of the fixed baffle plate 21 is overlappingly connected to the second connection portion 4 to prevent the leakage via concave-convex mating.

Furthermore, the first connection portion 3 and the second connection portion 4 are both made of an insulative material, which effectively prevents free movement of electrons between the moveable baffle plate 22 and the adjacent baffle wall to affect accuracy of the capacitance measurement.

Preferably, the moveable baffle plate 22 is rectangular, and a local capacitance measuring method is used to ensure integrity of the baffle mechanism 2. The number of the moveable baffle plates 22 of the baffle mechanism 2 may be one or plural according to needs.

To prevent waste of resources and save the cost, an individual moveable baffle plate 22 serving as a measurement window is provided on a currently-available massive baffle mechanism 2, and the adjacent baffle wall and the moveable baffle plate 22 are resepctively connected to the capacitance measurement device 1 via a lead wire so as to accurately detect the service life of the baffle mechanism 2, achieve precise management of the apparatus and reduce the operation cost. The capacitance measurement device 1 used by the detection device may be a multimeter or a capacitance meter or an electrical bridge testing instrument for measuring a capacitance which will be described in detail as follows.

The multimeter comprises three major portions, namely, a meter head, a measuring circuit and a changeover switch. In use, the adjacent baffle wall and the moveable baffle plate 22 are respectively communicated with a measuring circuit via a lead wire. The changeover switch is regulated to a capacitance measuring state, and then a capacitance value may be read on the meter head. The multimeter is advantageous in high sensitivity, high precision, clear display, a strong overload capacity and portability.

The capacitance meter comprises an integrated circuit capable of directly driving a microprocessor of an LCD and a double integral A/D converter, and a digital display drive of a high resolution and a high precision. The capacitance meter is a smart-type, stable-performance and highly reliable capacitance measurement tool. The adjacent baffle wall and the moveable baffle plate 22 are respectively connected to a capacitance input receptacle or terminals via a lead wire, and then adjust a measuring range to measure.

In the electrical bridge testing instrument, the adjacent baffle wall and the moveable baffle plate 22 are respectively communicated with a capacitance terminal of the electrical bridge testing instrument via a lead wire to achieve precise capacitance measurement.

The working procedure of the detection device according to the present disclosure includes the following steps: a first step of pivoting the moveable baffle plate to a position parallel with the adjacent baffle wall when the vacuum coating apparatus is idle; a second step of connecting the back side of the moveable baffle plate and the back side of the adjacent baffle wall which are parallel with each other to the multimeter or capacitance meter or electrical bridge testing instrument respectively via the lead wire; a third step of measuring and recording the capacitance between the moveable baffle plate and the adjacent baffle wall; a fourth step of calculating the spacing between the moveable baffle plate and the adjacent baffle wall after coating according to the capacitance calculating formula $C=\in S/d$, wherein $\in$ is a dielectric constant of a medium between polar plates, S is a polar plate area, and d is a distance between polar plates. A thickness of the thin film already adhered on the baffle mechanism may be calculated by comparing the resultant spacing with a spacing between the moveable baffle plate and the adjacent baffle wall before the coating. A fifth step of pivoting the independent moveable baffle plate to close with the fixed baffle plate to achieve the integrity of the baffle mechanism when the vacuum coating apparatus operates.

To conclude, the baffle mechanism of the detection device of the present disclosure is a closed structure encompassed by a plurality of baffle walls, wherein at least one baffle wall comprises a fixed baffle plate and a moveable baffle plate. The moveable baffle plate is pivotable about the fixed baffle plate. The moveable baffle plate, after pivoting, may get parallel with an adjacent baffle wall. The adjacent baffle wall and the moveable baffle plate are respectively connected to the capacitance measurement device, and the capacitance measurement device is used to measure the capacitance between the adjacent baffle wall and the moveable baffle plate. The detection device may accurately detect the service life of the baffle mechanism and achieve precise management of the apparatus. The detection device is simple in structure and may not greatly increase the manufacture and operation costs. The precise management of the service life of the baffle mechanism may be performed without opening the chamber, thus the operation cost of apparatuses in production line may be effectively reduced.

Embodiments of the present disclosure are presented for the sake of illustration and description, and not intended to exhaust embodiments and limit the present disclosure to the disclosed forms. Many modification and variations are obvious for those having ordinary skill in the art. Embodiments are selected and described to better illustrate principles and actual application of the present disclosure and enable those having ordinary skill in the art to understand the present disclosure and thereby design various embodiments with diverse modifications suitable for specific use.

The invention claimed is:

1. A detection system for detecting a service life of a baffle mechanism in a chamber for vacuum coating, comprising:
   the chamber for vacuum coating;
   a coating material generating device disposed inside the chamber;
   a capacitance measurement device; and
   a baffle mechanism located between an inner wall of the chamber and the coating material generating device;
   wherein the baffle mechanism is for preventing coating materials generated by the coating material generating device from directly depositing on the inner wall of the chamber;
   wherein the baffle mechanism is a closed structure encompassed by a plurality of baffle walls; and
   wherein an object to be coated and the coating material generating device are located within the closed structure of the baffle mechanism, the object to be coated being positioned between the baffle mechanism and the coating material generating device, at least one baffle wall comprises a fixed baffle plate and a moveable baffle plate that is pivotable about the fixed baffle plate to a pivoted position that is substantially parallel with an adjacent baffle wall, the adjacent baffle wall and the moveable baffle plate are respectively connected to the capacitance measurement device, and the capacitance measurement device is outside of the baffle mechanism and used to measure the capacitance between the adjacent baffle wall and the moveable baffle plate in the pivoted position.

2. The detection device according to claim 1, wherein the baffle mechanism is in shape of a cube, the fixed baffle plate and the moveable baffle plate are both located at the top or both located at the bottom of the cube, and the moveable baffle plate, after pivoting 90° about the fixed baffle plate, is substantially parallel with the adjacent baffle wall.

3. The detection device according to claim 1, wherein an edge of the moveable baffle plate includes a first connection portion and a second connection portion, during closing the baffle mechanism, the moveable baffle plate is pivoted to connect the first connection portion to an end of the fixed baffle plate and connect the second connection portion to another end of the fixed baffle plate.

4. The detection device according to claim 3, wherein a seal strip is disposed on the first connection portion, and located at a slit between the fixed baffle plate and the moveable baffle plate.

5. The detection device according to claim 3, wherein the first connection portion and the second connection portion are both made of an insulative material.

6. The detection device according to claim 3, wherein the moveable baffle plate is rectangular.

7. The detection device according to claim 1, wherein the adjacent baffle wall and the moveable baffle plate are respectively connected to the capacitance measurement device via a lead wire.

8. The detection device according to claim 7, wherein the capacitance measurement device is a multimeter, a capacitance meter or an electrical bridge testing instrument for measuring capacitance.

9. The detection device according to claim 1, wherein a thin film is deposited on an interior surface of at least one of the baffle walls.

10. The detection device according to claim 1, wherein the coating material generating device only generates material when the moveable baffle plate is in a close position.

* * * * *